United States Patent
Kuno et al.

(10) Patent No.: US 9,645,515 B2
(45) Date of Patent: *May 9, 2017

(54) ELECTROPHOTOGRAPHIC PHOTOSENSITIVE MEMBER AND MANUFACTURING METHOD THEREOF, PROCESS CARTRIDGE AND ELECTROPHOTOGRAPHIC APPARATUS, AND PHTHALOCYANINE CRYSTAL AND MANUFACTURING METHOD THEREOF

(71) Applicant: CANON KABUSHIKI KAISHA, Tokyo (JP)

(72) Inventors: Junpei Kuno, Mishima (JP); Tsutomu Nishida, Mishima (JP); Masato Tanaka, Tagata-gun (JP); Masataka Kawahara, Mishima (JP); Kaname Watariguchi, Yokohama (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/689,341

(22) Filed: Apr. 17, 2015

(65) Prior Publication Data

US 2015/0316864 A1 Nov. 5, 2015

(30) Foreign Application Priority Data

Apr. 30, 2014 (JP) .................................. 2014-094020
Mar. 31, 2015 (JP) .................................. 2015-072648

(51) Int. Cl.
*G03G 5/047* (2006.01)
*G03G 5/06* (2006.01)
(Continued)

(52) U.S. Cl.
CPC ......... *G03G 5/0662* (2013.01); *C07D 487/22* (2013.01); *C07F 5/003* (2013.01);
(Continued)

(58) Field of Classification Search
CPC ........................... G03G 5/0696; G03G 5/0525
See application file for complete search history.

(56) References Cited

U.S. PATENT DOCUMENTS 5,194,088 A 3/1993 Babler et al.
5,834,149 A 11/1998 Tambo et al.
(Continued)

FOREIGN PATENT DOCUMENTS

JP 5-222314 A 8/1993
JP 7-331107 A 12/1995
(Continued)

OTHER PUBLICATIONS

U.S. Appl. No. 14/721,307, filed May 26, 2015. Inventor: Masataka Kawahara, et al.
(Continued)

*Primary Examiner* — Peter Vajda
(74) *Attorney, Agent, or Firm* — Fitzpatrick Cella Harper and Scinto (57) ABSTRACT

An electrophotographic photosensitive member capable of outputting an image with suppressed positive ghosting, and a process cartridge and an electrophotographic apparatus each having the electrophotographic photosensitive member are provided. The electrophotographic photosensitive member has a photosensitive layer including a phthalocyanine crystal in which the compound represented by the formula (1) is contained, wherein the content of the compound represented by the formula (1) is 0.1% by mass or more and 1.7% by mass or less based on the phthalocyanine crystal.

18 Claims, 7 Drawing Sheets

(51) Int. Cl.

| | |
|---|---|
| *C07F 5/00* | (2006.01) |
| *C07D 487/22* | (2006.01) |
| *C30B 29/54* | (2006.01) |
| *G03G 15/00* | (2006.01) |
| *G03G 21/18* | (2006.01) |
| *G03G 5/00* | (2006.01) |
| *G03G 5/04* | (2006.01) |
| *G03G 5/05* | (2006.01) |

(52) U.S. Cl.
CPC ............... *C30B 29/54* (2013.01); *G03G 5/00* (2013.01); *G03G 5/04* (2013.01); *G03G 5/05* (2013.01); *G03G 5/06* (2013.01); *G03G 5/0696* (2013.01); *G03G 15/00* (2013.01); *G03G 15/75* (2013.01); *G03G 21/18* (2013.01)

(56) References Cited

U.S. PATENT DOCUMENTS

| | | |
|---|---|---|
| 6,245,472 B1 | 6/2001 | Tanaka |
| 6,472,524 B2 | 10/2002 | Tanaka |
| 7,381,512 B2 | 6/2008 | Hongo et al. |
| 8,518,615 B2 | 8/2013 | Tanaka |
| 8,974,991 B2 | 3/2015 | Kawahara et al. |
| 2012/0322998 A1 | 12/2012 | Hongo et al. |
| 2014/0170540 A1 | 6/2014 | Tanaka |
| 2014/0170542 A1 | 6/2014 | Tanaka |
| 2015/0093694 A1 | 4/2015 | Watariguchi et al. |
| 2015/0309427 A1* | 10/2015 | Kawahara ............ G03G 5/0696 430/56 |
| 2015/0309428 A1* | 10/2015 | Kawahara ............ G03G 5/0662 430/56 |

FOREIGN PATENT DOCUMENTS

| | | |
|---|---|---|
| JP | 9-241525 A | 9/1997 |
| JP | 2793020 B2 | 9/1998 |
| JP | 2002-235014 A | 8/2002 |
| JP | 4635461 B2 | 2/2011 |
| JP | 2011-94101 A | 5/2011 |
| JP | 5266693 B2 | 8/2013 |

OTHER PUBLICATIONS

U.S. Appl. No. 14/722,985, filed May 27, 2015. Inventor: Masataka Kawahara, et al.
U.S. Appl. No. 14/730,482, filed Jun. 4, 2015. Inventor: Masato Tanaka, et al.
U.S. Appl. No. 14/689,364, filed Apr. 17, 2015. Inventor: Junpei Kuno, et al.
U.S. Appl. No. 14/677,855, filed Apr. 2, 2015. Inventor: Tsutomu Nishida, et al.
U.S. Appl. No. 14/740,941, filed Jun. 16, 2015. Inventor: Masato Tanaka, et al.
U.S. Appl. No. 14/680,040, filed Apr. 6, 2015. Inventor: Masato Tanaka, et al.

* cited by examiner

ELECTROPHOTOGRAPHIC PHOTOSENSITIVE MEMBER AND MANUFACTURING METHOD THEREOF, PROCESS CARTRIDGE AND ELECTROPHOTOGRAPHIC APPARATUS, AND PHTHALOCYANINE CRYSTAL AND MANUFACTURING METHOD THEREOF

BACKGROUND OF THE INVENTION

Field of the Invention

The present invention relates to an electrophotographic photosensitive member and a manufacturing method thereof, a process cartridge and an electrophotographic apparatus, and a phthalocyanine crystal and a manufacturing method thereof.

Description of the Related Art

An electrophotographic photosensitive member for use in an electrophotographic apparatus such as a copier and a laser beam printer is required to have sufficient sensitivity to the light for image exposure. It is known that an azo pigment and a phthalocyanine pigment for use as a charge generating substance have high sensitivity to the light in a wide range of wavelength.

A higher quality image typically including a colored image has been increasingly required in recent years, with increased demand for a half-tone image and a solid image of a photograph, as a typical example. The allowable range, for example, for a so-called positive ghost image, i.e. a phenomenon that an area exposed to light in a sheet of image has high density in a half-tone image, has been distinctly severer in comparison with the allowable range for a monochrome printer or a monochrome copier. It is presumed that the ghost images occur because electrons tend to remain in the charge generation layer to make a memory after injection of positive holes as one of carriers generated from a charge generating substance.

In Japanese Patent Application Laid-Open No. H07-331107, a hydroxygallium phthalocyanine crystal including at least one polar organic solvent selected from the group consisting of a compound having an amide group, a compound having a sulfoxide group, and an organic amine is disclosed.

In Japanese Patent Application Laid-Open No. 2002-235014, a hydroxygallium phthalocyanine crystal obtained by milling treatment using N-methylformamide, N-methylacetamide, and N-methylpropionamide is disclosed.

SUMMARY OF THE INVENTION

As a result of study by the present inventors, it was found that the hydroxygallium phthalocyanine crystal disclosed in Japanese Patent Application Laid-Open No. H07-331107 has insufficient improvement in suppression of positive ghosting. It was also found that the hydroxygallium phthalocyanine crystal disclosed in Japanese Patent Application Laid-Open No. 2002-235014 has room for improvement in suppression of positive ghosting, since there is no description on the content of the compounds with no Examples.

One embodiment of the present invention is directed to providing an electrophotographic photosensitive member capable of outputting an image having few defects with suppressed positive ghosting, and a manufacturing method thereof. Another embodiment of the present invention is directed to providing a process cartridge and an electrophotographic apparatus each having the electrophotographic photosensitive member.

A still another embodiment of the present invention is directed to providing a phthalocyanine crystal which contains a specific amide compound in the crystal, and a manufacturing method thereof.

According to one aspect of the present invention, there is provided an electrophotographic photosensitive member including: a support and a photosensitive layer formed on the support, wherein the photosensitive layer includes: a phthalocyanine crystal in which a compound represented by the following formula (1) is contained, (1)

wherein, in the formula (1), X represents a hydrogen atom or an alkyl group having 1 or 2 carbon atoms, and wherein the content of the compound represented by the formula (1) is 0.1% by mass or more and 1.7% by mass or less based on a phthalocyanine in the phthalocyanine crystal.

According to another aspect of the present invention, there is provided a process cartridge which integrally supports: the electrophotographic photosensitive member, and at least one unit selected from the group consisting of a charging unit, a developing unit, a transfer unit, and a cleaning unit, the cartridge being detachably mountable to a main body of an electrophotographic apparatus.

According to further aspect of the present invention, there is provided an electrophotographic apparatus having the electrophotographic photosensitive member, with a charging unit, an exposing unit, a developing unit and a transfer unit.

According to further aspect of the present invention, there is provided a phthalocyanine crystal in which the compound represented by the formula (1) is contained, and the content of the compound represented by the formula (1) is 0.1% by mass or more and 1.7% by mass or less based on a phthalocyanine in the phthalocyanine crystal.

According to further aspect of the present invention, there is provided a manufacturing method of the phthalocyanine crystal in which a compound represented by the formula (1) is contained, including: transforming the phthalocyanine crystal by adding the compound represented by the formula (1) to a phthalocyanine followed by milling treatment.

According to further aspect of the present invention, there is provided a manufacturing method of an electrophotographic photosensitive member having a support and a photosensitive layer formed on the support, including: manufacturing the phthalocyanine crystal by the manufacturing method of the phthalocyanine crystal, and forming a coating film from a coating liquid for forming the photosensitive layer which contains the phthalocyanine crystal, and drying the coating film to form the photosensitive layer.

The present invention can provide an electrophotographic photosensitive member with a positive ghost image being suppressed, a manufacturing method thereof, and a process cartridge and an electrophotographic apparatus each having the electrophotographic photosensitive member.

The present invention can further provide a phthalocyanine crystal in which a specific amide compound is contained, and a manufacturing method thereof.

Further features of the present invention will become apparent from the following description of exemplary embodiments with reference to the attached drawings.

DESCRIPTION OF THE EMBODIMENTS

Preferred Embodiments of the Present Invention will now be described in detail in accordance with the accompanying drawings.

As described above, the electrophotographic photosensitive member of the present invention includes a support and a photosensitive layer formed on the support. The photosensitive layer includes a phthalocyanine crystal in which a compound represented by the following formula (1) is contained, and the content of the compound represented by the formula (1) is 0.1% by mass or more and 1.7% by mass or less based on a phthalocyanine in the phthalocyanine crystal.

(1)

wherein, in the formula (1), X represents a hydrogen atom or an alkyl group having 1 or 2 carbon atoms; preferably X is a hydrogen atom.

The phthalocyanine in a phthalocyanine crystal means a portion of the phthalocyanine crystal in which a compound represented by the formula (1) is contained, excluding the compound represented by the formula (1). The content of the compound represented by the formula (1) can be obtained by NMR measurement, and the details will be described in the following.

Examples of the phthalocyanine for use to compose a phthalocyanine crystal in which a compound represented by the formula (1) is contained include a phthalocyanine such as a non-metal phthalocyanine and a metal phthalocyanine which may have an axial ligand, which may further have a substituent. Although oxytitanium phthalocyanine and gallium phthalocyanine, in particular, have excellent sensitivity characteristics among them, the generated photo carriers tend to remain in the photosensitive layer, easily causing problems such as positive ghosting, to which the present invention can be effectively applied.

Examples of the gallium phthalocyanine include a gallium phthalocyanine molecule of which gallium atom has an axial ligand of a halogen atom, a hydroxy group or an alkoxy group. The phthalocyanine ring may include a substituent such as a halogen atom.

Among gallium phthalocyanine crystals, a hydroxygallium phthalocyanine crystal, a chlorogallium phthalocyanine crystal, a bromo-gallium phthalocyanine crystal and an iodo-gallium phthalocyanine crystal, having excellent sensitivity, are preferred. A hydroxygallium phthalocyanine crystal is preferred in particular. The hydroxygallium phthalocyanine crystal includes a gallium atom having an axial ligand of hydroxy group. In a chlorogallium phthalocyanine crystal, a gallium atom has a chlorine atom as an axial ligand. The bromo-gallium phthalocyanine crystal includes a gallium atom having an axial ligand of bromine atom. The iodo-gallium phthalocyanine crystal includes a gallium atom having an axial ligand of iodine atom.

Further, from the viewpoint of suppressing image defects due to ghosting, a hydroxygallium phthalocyanine crystal having peaks at Bragg angles 2θ of 7.4°±0.3° and 28.3°±0.3° in X-ray diffraction with CuKα radiation is more preferred.

The content of the compound represented by the formula (1) contained in the phthalocyanine in the phthalocyanine crystal is 0.1% by mass or more and 1.7% by mass or less. A content of 0.2% by mass or more and 1.2% by mass or less is more preferred.

In the phthalocyanine crystal which contains a compound represented by the formula (1) in the crystal, the compound represented by the formula (1) is incorporated into the crystal.

It is presumed that when the compound represented by the formula (1) is contained in a phthalocyanine crystal, charge-trapping sites are offset by the polarity in the molecule of a solvent, so that electrons hardly remain in the charge generation layer. It is presumed that the electrophotographic photosensitive member of the present invention thereby suppresses ghosting.

A manufacturing method of a phthalocyanine crystal which contains a compound represented by the formula (1) in the crystal is described below.

The phthalocyanine crystal including a phthalocyanine crystal in which a compound represented by the following formula (1) is contained is obtained by transforming the phthalocyanine crystal by adding the compound represented by the formula (1) to a phthalocyanine followed by milling treatment. The phthalocyanine for use in the milling treatment can be a phthalocyanine obtained by an acid-pasting method.

The milling treatment is a treatment in a milling device such as a sand mill and a ball mill, using dispersion material such as glass beads, steel beads and alumina balls. The amount of the compound represented by the formula (1) to be added in milling treatment can be 5 to 30 times the amount of the phthalocyanine by mass.

As the transformation solvent other than the compound represented by the formula (1), for example, an amide solvent such as N,N-dimethylformamide, N,N-dimethylacetoamide, and 1-methyl-2-pyrolidone, a halogen solvent such as chloroform, an ether solvent such as tetrahydrofuran, and a sulfoxide solvent such as dimethylsulfoxide may be used in combination. The amount of the solvent used can be 5 to 30 times the amount of phthalocyanine by mass.

The time period for the milling treatment can be 200 hours or more. A time period of 200 hours or more and 2000 hours or less is more preferred.

Whether the phthalocyanine crystal of the present invention contains a compound represented by the formula (1) in the crystal was determined by measuring the produced phthalocyanine crystal by NMR measurement and analyzing the data, in the present invention.

The X-ray diffraction analysis and the NMR measurement of the phthalocyanine crystal of the present invention were performed under the following conditions.

[Powder X-Ray Diffraction Analysis]
Measurement instrument: X-ray diffraction analyzer RINT-TTRII made by Rigaku Corporation
X-ray tube: Cu
X-ray tube voltage: 50 KV
X-ray tube current; 300 mA
Scanning method: 2θ/θ scan
Scanning rate: 4.0°/min
Sampling interval: 0.02°
Starting angle (2θ): 5.0°
Stopping angle (2θ): 40.0°
Attachment: Standard sample holder
Filter: non-use
Incident monochrome: in-use
Counter monochrometer: non-use
Divergence slit: open
Vertical divergence limiting slit: 10.00 mm
Scattering slit: open
Light receiving slit: open
Flat plate monochrometer: in use
Counter: scintillation counter

[$^1$H-NMR Measurement]
Measurement instrument: Trade name: AVANCE III 500 made by Bruker
Solvent: deuterium sulfate ($D_2SO_4$)
Cumulated number: 2000

The X of the compound (1) contained in the hydroxygallium phthalocyanine crystal can be a hydrogen atom from the viewpoint of suppressing the ghosting.

Further, the hydroxygallium phthalocyanine crystal having a local maximal peak in the range of 642 to 650 nm in an optical absorption spectrum is more preferred from the viewpoint of suppressing the ghosting.

Further, the hydroxygallium phthalocyanine crystal having a local maximal peak in the range of 810 to 820 nm in an optical absorption spectrum is more preferred from the viewpoint of suppressing the ghosting. Additionally, the local maximal peak means a peak in which a change of absorbance moves from increase to decrease in an optical absorption spectrum.

The measurement of the optical absorption spectrum of a hydroxygallium phthalocyanine crystal was performed under the following conditions. A charge generation layer (photosensitive layer) only was formed on a polyester film (trade name: LUMIRROR, model number: T 60, thickness: 100 μm, made by Toray Industries, Inc.) was used as a measurement sample. The forming method thereof is described in the following.

A sand mill with use of glass beads having a diameter of 1 mm was charged with 10 parts of the hydroxygallium phthalocyanine crystal of the present invention, 5 parts of polyvinyl butyral (trade name: ESLEC BX-1, made by Sekisui Chemical Co., Ltd.), and 250 parts of cyclohexanone, which are subjected to dispersion treatment for 1 hour, so that a dispersion liquid is prepared. To the dispersion liquid, 250 parts of ethyl acetate was added to dilute it, thereby preparing a dispersion liquid of hydroxygallium phthalocyanine crystal. The dispersion liquid was applied onto the polyester film so as to form a coating film. The produced coating film was dried, so that a dispersion film of hydroxygallium phthalocyanine crystal having a thickness of 0.15 μm was formed.

The produced dispersion film was subjected to measurement of optical absorption spectrum using the following measurement device.

<Optical Absorption Spectrum>
Measurement device for use: Ultraviolet-visible spectrophotometer JASCO V-570, made by JASCO Corporation.
Measurement mode: Abs spectrometry
Response: fast
Band width: 2.0 nm Band width in the near-infrared: 8.0 nm
Scanning rate: 200 nm/min
Starting wavelength: 1000 nm
Stopping wavelength: 300 nm
Data acquisition interval: 0.5 nm The phthalocyanine crystal which contains a compound represented by the formula (1) of the present invention in the crystal has an excellent function as a photoconductive material, and is applicable to a solar cell, a sensor, a switching device and the like, in addition to an electrophotographic photosensitive member.

The use of the phthalocyanine crystal in which a compound represented by the formula (1) is contained as a charge generating substance of an electrophotographic photosensitive member is described in the following.

The electrophotographic photosensitive member of the present invention includes a support and a photosensitive layer formed on the support. A photosensitive layer includes: a single-layer type photosensitive layer having a single layer which contains a charge generating substance and a charge transporting substance; and a laminate type photosensitive layer having a lamination structure of a charge generation layer which contains a charge generating substance and a charge transport layer which contains a charge transporting substance. In particular, a laminate type photosensitive layer having a charge generation layer and a charge transport layer formed on a charge generation layer is preferred.

A support for use in the electrophotographic photosensitive member of the present invention can have electrical conductivity (conductive support). For example, the support made of metal or alloy such as aluminum, aluminum alloy, copper, zinc, stainless steel, vanadium, molybdenum, chromium, titanium, nickel, indium, gold, and platinum can be used. Alternatively, a plastic (e.g. polyethylene, polypropylene, polyvinyl chloride, polyethylene terephthalate, acrylic resin, and polyfluoroethylene) coated with a vacuum deposited layer of aluminum, aluminum alloy, indium oxide, tin oxide, or indium oxide-tin oxide alloy, a support including a plastic or the support coated with conductive particles (e.g. aluminum particles, titanium oxide particles, tin oxide particles, zinc oxide particles, carbon black, and silver particles) together with a binder resin, a support formed of a plastic or paper impregnated with conductive particles, and a plastic having a conductive polymer may be used.

In the electrophotographic photosensitive member of the present invention, an undercoat layer (also referred to as a barrier layer or an intermediate layer) having a barrier function and an adhesive function may be disposed between the support and the photosensitive layer. An undercoat layer may be formed by forming a coating film from a coating liquid for forming an undercoat layer including a mixture of a binder resin and a solvent, and then by drying the coating film.

The binder resin can be made from a raw material such as polyvinyl alcohol, polyethylene oxide, ethyl cellulose, methyl cellulose, casein, polyamide (e.g. nylon 6, nylon 66, nylon 610, a copolymer nylon, N-alkoxymethylated nylon), polyurethane, glue, aluminum oxide and gelatin. The undercoat layer has a film thickness of 0.1 to 10 µm, preferably 0.5 to 5 µm. Further, a conductive layer containing a conductive particle may be provided between a support and an intermediate layer.

In the case of forming a single-layer type photosensitive layer, a phthalocyanine crystal in which a compound represented by the formula (1) is contained is used as a charge generating substance, which is blended in a binder resin solution together with a charge transport substance for preparation of a coating liquid for forming the photosensitive layer. The coating liquid for forming the photosensitive layer is applied onto the support to form a coating film, which is then dried to form the photosensitive layer.

In the case of forming a laminate type photosensitive layer, the charge generation layer can be formed by: applying a coating liquid for forming a charge generation layer, obtained by dispersing a phthalocyanine crystal in which a compound represented by the formula (1) is contained, into a binder resin solution; and drying the produced coating film. Alternatively the charge generation layer may be formed by vapor deposition.

In the case of forming a laminate type photosensitive layer, the charge transport layer can be formed by applying a coating liquid for forming a charge transport layer obtained by dissolving a charge transport substance and a binder resin onto the charge generation layer, and drying the produced coating film.

Examples of the charge transporting substance include a triarylamine-based compound, a hydrazine-based compound, a stilbene-based compound, a pyrazoline-based compound, an oxazole-based compound, a thiazole-based compound and a triallylmethane-based compound.

Examples of the binder resin for use in the single-layer type photosensitive layer, the charge generation layer and the charge transport layer include the following resins. For example, a resin such as polyester, an acrylic resin, polyvinylcarbazole, a phenoxy resin, polycarbonate, polyvinylbutyral, polystyrene, polyvinyl acetate, polysulfone, polyallylate, vinylidene chloride, acrylonitrile copolymer and polyvinyl benzal is used.

Examples of the application method to form a photosensitive layer include dip coating, spray coating, spinner coating, bead coating, blade coating and beam coating.

A single-layer type photosensitive layer can have a film thickness of 4 to 40 µm, more preferably 5 to 25 µm.

The charge generation layer of a laminate type photosensitive layer can have a film thickness of 0.01 to 10 µm, more preferably 0.1 to 3 µm. The charge transport layer can have a film thickness of 4 to 40 µm, more preferably 5 to 25 µm.

In the case of a laminate type photosensitive layer, the content of the charge generating substance in a charge generation layer is preferably 20 to 90% by mass, more preferably 50 to 80% by mass, based on the total mass of the charge generation layer. Further, the content of the charge transport substance in a charge transport layer is preferably 20 to 80% by mass, more preferably 30 to 70% by mass, based on the total mass of the charge transport layer.

The content of the charge generating substance of a single-layer type photosensitive layer can be 3 to 30% by mass relative to the total mass of the photosensitive layer. The content of the charge transporting substance can be 30 to 70% by mass relative to the total mass of the photosensitive layer.

The phthalocyanine crystal of the present invention may be mixed with another charge generating substance for use as charge generating substance. In that case, the content of the phthalocyanine crystal of the present invention can be 50% by mass or more relative to the total charge generating substance.

A protective layer may be provided on the photosensitive layer on an as needed basis. The protective layer may be formed by forming a coating film from coating liquid for forming a protective layer obtained by dissolving a binder resin in a solvent, and drying the coating film. Examples of the binder resin include polyvinylbutyral, polyester, polycarbonate (e.g., polycarbonate Z and modified polycarbonate), nylon, polyimide, polyallylate, polyurethane, a styrene-butadiene copolymer, a styrene-acrylic acid co-polymer and a styrene-acrylonitrile co-polymer. The protective layer can have a film thickness of 0.05 to 20 µm.

The protective layer may contain conductive particles or an ultraviolet absorbing agent. Examples of the conductive particles include metal oxide particles such as tin oxide particles.

Figure 1:
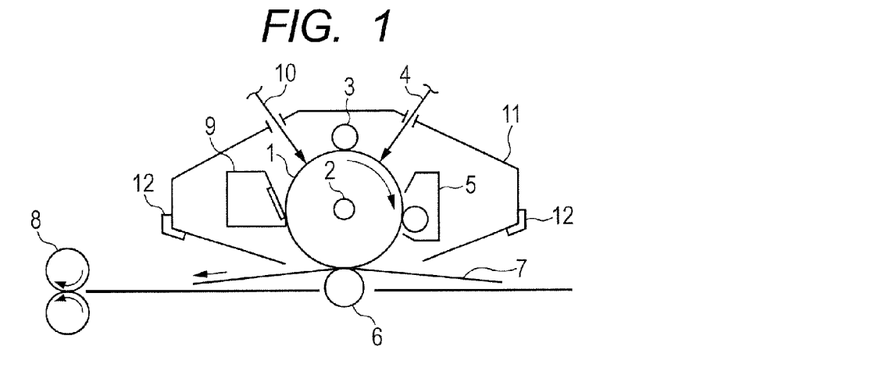
FIG. 1 is a schematic view of an electrophotographic apparatus provided with a process cartridge having an electrophotographic photosensitive member of the present invention.

FIG. 1 is a schematic view of an electrophotographic apparatus provided with a process cartridge having an electrophotographic photosensitive member of the present invention.

An electrophotographic photosensitive member 1 having a cylindrical shape (drum shape), is rotation driven around an axis 2 at a predetermined circumferential speed (process speed) in an arrow direction.

The surface of the electrophotographic photosensitive member 1 is electrostatically charged to a positive or negative predetermined potential with a charging unit 3 during in a rotation process. Subsequently the charged surface of the electrophotographic photosensitive member 1 is irradiated with image exposing light 4 from an image exposing unit (not drawn in figure) so as to form an electrostatic latent image corresponding to objective image information. The image exposing light 4 are intensity-modulated in response to the time-series electric digital image signals of objective image information, outputted from, for example, an image exposing unit for slit exposing or exposing with scanning laser beams.

The electrostatic latent image formed on the surface of the electrophotographic photosensitive member 1 is developed (normal development or reversal development) with toner stored in a developing unit 5 so as to form a toner image on the surface of the electrophotographic photosensitive member 1. The toner image formed on the surface of the electrophotographic photosensitive member 1 is transferred to a transfer material 7 with a transfer unit 6. On this occasion, a bias voltage having a polarity reversal of the charge retained on the toner is applied to the transfer unit 6 from a bias power supply (not drawn in figure). A transfer material 7 of paper is taken out from a paper feeding part (not drawn in figure) so as to be fed between the electrophotographic photosensitive member 1 and the transfer unit 6 in synchronization with the rotation of the electrophotographic photosensitive member 1.

The transfer material 7 having a toner image transferred from the electrophotographic photosensitive member 1 is separated from the surface of the electrophotographic photosensitive member 1 and transported to an image fixation unit 8 for the fixation of the toner image. An image formed object (print or copy) is thus printed out from an electrophotographic apparatus.

After transfer of the toner image to the transfer material 7, the surface of the electrophotographic photosensitive member 1 is cleaned with a cleaning unit 9 to remove attached material such as toner (remaining toner after transfer). In a recently developed cleaner-less system, toner may be directly removed after transfer with a development apparatus or the like. Subsequently the surface of the electrophotographic photosensitive member 1 is neutralized with pre-exposing light 10 from a pre-exposing unit (not drawn in figure) and then repeatedly used for image formation. The pre-exposing unit is not necessarily required for a contact charging unit 3 having a charging roller.

In the present invention, a plurality of components including the electrophotographic photosensitive member 1, the charging unit 3, the developing unit 5, the transfer unit 6, and the cleaning unit 9 may be accommodated in a container so as to be integrally supported, thereby forming a process cartridge. The process cartridge can be configured to be detachable to an electrophotographic apparatus body. For example, At least one selected from a charging unit 3, a developing unit 5 and a cleaning unit 9 is integrally supported together with the electrophotographic photosensitive member 1 so as to form a cartridge. The cartridge constitutes a process cartridge 11 detachable to an electrophotographic apparatus body with a guiding unit 12 such as a rail of the electrophotographic apparatus body.

Image exposing light 4 may be reflected beams from or transmitted beams through a sheet of manuscript for an electrophotographic apparatus such as a copy machine and a printer. Alternatively, image exposing light 4 may be radiated beams produced by scanning of laser beams, driving of an LED array or driving of a liquid crystal shutter array in response to signals from a manuscript reading sensor.

The electrophotographic photosensitive member 1 of the present invention can be widely used in an electrophotography application field such as a laser beam printer, a CRT printer, an LED printer, a FAX, a liquid crystal printer and a laser engraving.

EXAMPLES

The present invention is described further in detail in reference to specific Examples in the following, although the present invention is not limited thereto. The film thickness of each of the layers of electrophotographic photosensitive members in Examples and Comparative Examples was obtained with an eddy-current film thickness meter (Fischerscope made by Fischer Instruments K.K.), or based on the specific gravity converted from a mass per unit area. In Examples, "part" means "part by mass".

Example 1-1

Hydroxygallium phthalocyanine was manufactured as follows, in the same way as in Example 1-1 subsequent to the synthesis example 1 described in Japanese Patent Application Laid-Open No. 2011-94101. Under nitrogen flow atmosphere, 5.46 parts of phthalonitrile and 45 parts of α-chloronaphthalene were fed into a reaction tank, then heated up to a temperature of 30° C., and maintained at the temperature. Subsequently, 3.75 parts of gallium trichloride was fed thereto at the temperature (30° C.). At the feeding time, the mixture liquid had a water content of 150 ppm. The temperature was then increased to 200° C. Under the nitrogen flow atmosphere, a reaction was caused at a temperature of 200° C. for 4.5 hours, which was then cooled to a temperature of 150° C. for filtering a product. The produced residue was dispersed and cleaned with N,N-dimethylformamide at a temperature of 140° C. for 2 hours, and then filtrated. The produced residue was cleaned with methanol and dried to produce 4.65 parts of chlorogallium phthalocyanine pigment (yield: 71%). Subsequently, 4.65 parts of the produced chlorogallium phthalocyanine pigment was dissolved in 139.5 parts of concentrated sulfuric acid at a temperature of 10° C., and instilled into 620 parts of iced water under agitation for reprecipitation. The product was filtrated with a filter press. Subsequently, the produced wet cake (residue) was dispersed and cleaned with 2% ammonia water, and filtrated with a filter press. Subsequently, the produced wet cake (residue) was dispersed and cleaned with ion-exchange water, and then filtration with a filter press was repeated 3 times. Then, hydroxygallium phthalocyanine (hydrous hydroxygallium phthalocyanine) having a solid content of 23% was produced. The produced hydroxygallium phthalocyanine (hydrous hydroxygallium phthalocyanine) in an amount of 6.6 kg was irradiated by microwave with a hyper dryer (trade name: HD-06R, frequency (oscillation frequency): 2,455 MHz±15 MHz, made by Biocon Japan Ltd.) so as to be dried.

Thus produced hydroxygallium phthalocyanine in an amount of 0.5 parts and a compound (1) represented by the following formula Compound (1)

Figure 2:
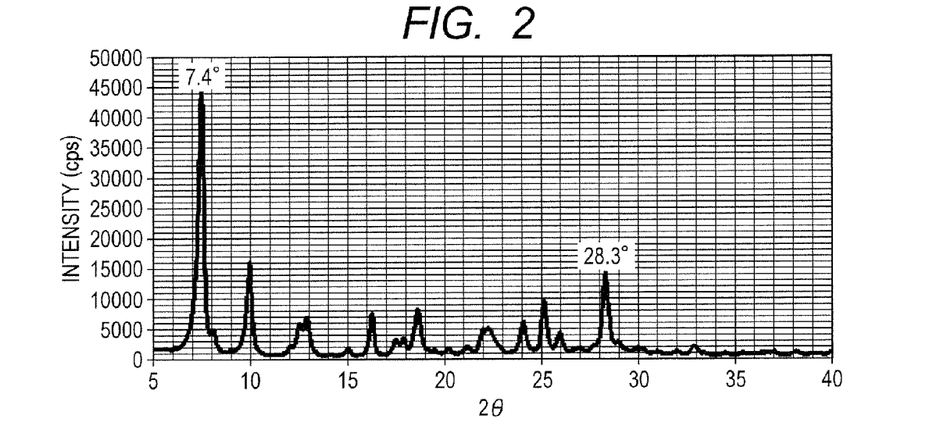
FIG. 2 is a powder X-ray diffraction chart of a hydroxygallium phthalocyanine crystal obtained in Example 1-1.

(product code: F0059, made by Tokyo Chemical Industry Co., Ltd.) in an amount of 9.5 parts are subjected to milling treatment together with 15 parts of glass beads having a diameter of 0.8 mm by a ball mill at room temperature (23° C.) for 600 hours. On this occasion, a standard bottle (product code: PS-6, made by Hakuyo Glass Co., Ltd.) was used as a container, which was rotated at 60 rpm. A gallium phthalocyanine crystal was produced from the dispersion liquid using tetrahydrofuran. In filtration, the strainer was sufficiently cleaned with tetrahydrofuran. The filter residue was vacuum dried so that 0.45 parts of hydroxygallium phthalocyanine crystal was obtained. The powder X-ray diffraction chart of the produced hydroxygallium phthalocyanine crystal is illustrated in FIG. 2. It is found that the crystal has peaks at Bragg angles 2θ±0.2° of 7.4° and 28.3° in CuKα characteristic X-ray diffraction. The crystal was dissolved in deuterosulfuric acid for $^1$H-NMR measurement, in which peaks derived from the compound (1) were observed other than the peaks derived from the phthalocyanine molecule. Since the compound (1) is liquid and compatible with tetrahydrofuran, it was found that the compound (1) was contained in the phthalocyanine crystal.

Figure 11:
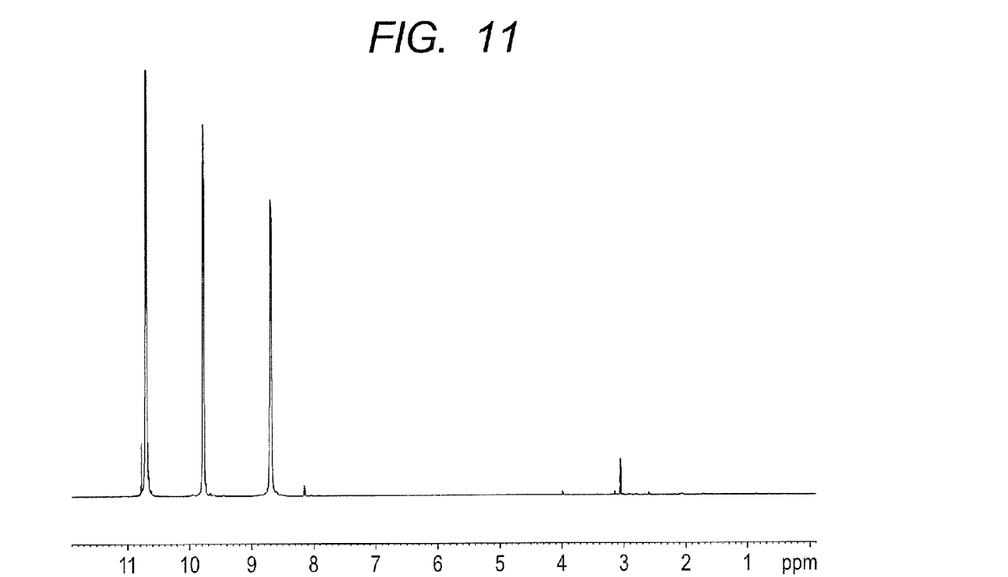
FIG. 11 is a chart illustrating a $^1$H-NMR spectrum of a hydroxygallium phthalocyanine crystal obtained in Example 1-1.
Figure 13:
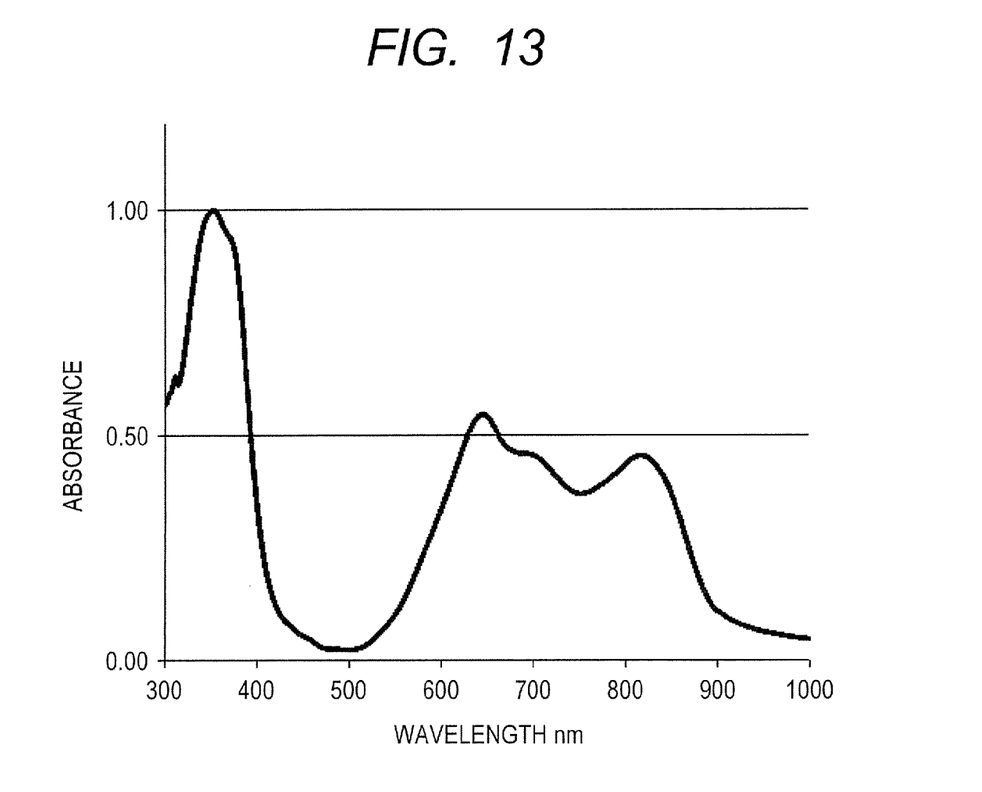
FIG. 13 is a chart illustrating an optical absorption spectrum of a hydroxygallium phthalocyanine crystal obtained in Example 1-1.

Based on conversion from the proton ratio, the content of the compound (1) based on phthalocyanine in the phthalocyanine crystal was 0.9% by mass. The $^1$H-NMR spectrum of the produced hydroxygallium phthalocyanine crystal is illustrated in FIG. 11. Using the produced hydroxygallium phthalocyanine crystal, the optical absorption spectrum was measured. The measurement results are illustrated in FIG. 13. The vertical line of FIG. 13 is standardized as maximum absorbance (Abs) is 1. The local maximal peak position in the wavelength range of 600 to 660 nm, and the local maximal peak position in the wavelength range of 800 to 900 nm are described in Table 1.

Example 1-2

A hydroxygallium phthalocyanine crystal was obtained in the same way as in Example 1-1, except that the milling treatment time was changed to 200 hours. The powder X-ray diffraction spectrum of the produced crystal was similar to that in FIG. 2, and the crystal had peaks at Bragg angles 2θ±0.2° of 7.4° and 28.3° in CuKα characteristic X-ray diffraction. As a result of the same NMR measurement as in Example 1-1, the compound (1) with a content of 1.7% by mass in the crystal was confirmed. Using the produced hydroxygallium phthalocyanine crystal, the optical absorption spectrum was measured. The local maximal peak position in the wavelength range of 600 to 660 nm, and the local maximal peak position in the wavelength range of 800 to 900 nm that were found are described in Table 1.

Example 1-3

A hydroxygallium phthalocyanine crystal was obtained in the same way as in Example 1-1, except that the milling treatment time was changed to 1000 hours. The powder X-ray diffraction spectrum of the produced crystal was similar to that in FIG. 2, and the crystal had peaks at Bragg angles 2θ±0.2° of 7.4° and 28.3° in CuKα characteristic X-ray diffraction. As a result of the same NMR measurement as in Example 1-1, the compound (1) with a content of 0.7% by mass in the crystal was confirmed. Using the produced hydroxygallium phthalocyanine crystal, the optical absorption spectrum was measured. The local maximal peak position in the wavelength range of 600 to 660 nm, and the local maximal peak position in the wavelength range of 800 to 900 nm that were found are described in Table 1.

Example 1-4

A hydroxygallium phthalocyanine crystal was obtained in the same manner as in Example 1-1, except that the milling treatment time was changed to 2000 hours. The powder X-ray diffraction spectrum of the produced crystal was similar to that in FIG. 2, and the crystal had peaks were shown at Bragg angles 2θ±0.2° of 7.4° and 28.3° in CuKα characteristic X-ray diffraction. As a result of the same NMR measurement as in Example 1-1, the compound (1) with a content of 0.55% by mass in the crystal was confirmed. Using the produced hydroxygallium phthalocyanine crystal, the optical absorption spectrum was measured. The local maximal peak position in the wavelength range of 600 to 660 nm, and the local maximal peak position in the wavelength range of 800 to 900 nm are described in Table 1.

Example 1-5

Figure 3:
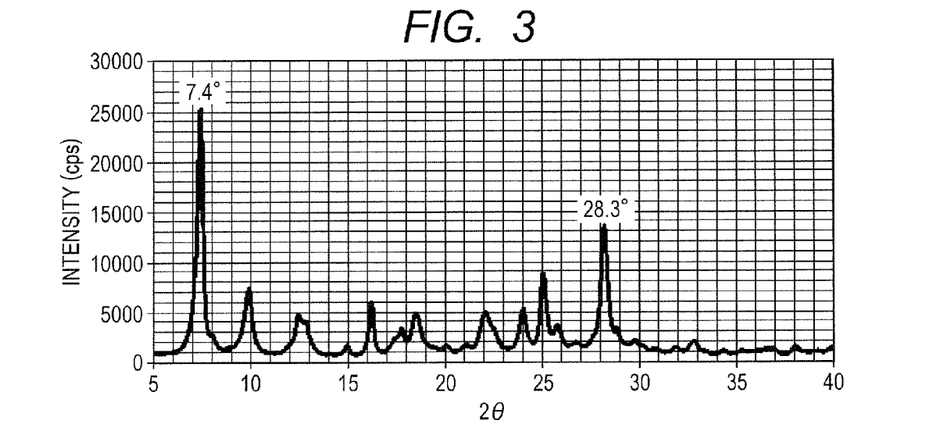
FIG. 3 is a powder X-ray diffraction chart of a hydroxygallium phthalocyanine crystal obtained in Example 1-5.

A hydroxygallium phthalocyanine crystal was obtained in the same manner as in Example 1-1, except that the milling treatment by a ball mill was changed to a milling treatment by a paint shaker (made by Toyo Seiki Seisaku-sho, Ltd.) for 8 hours. The powder X-ray diffraction spectrum of the produced crystal is illustrated in FIG. 3. It is found that the crystal has peaks at Bragg angles 2θ±0.2° of 7.4° and 28.3° in CuKα characteristic X-ray diffraction. As a result of the same NMR measurement as in Example 1-1, the compound (1) with a content of 1.6% by mass in the crystal was confirmed. Using the produced hydroxygallium phthalocyanine crystal, the optical absorption spectrum was measured. The local maximal peak position in the wavelength range of 600 to 660 nm, and the local maximal peak position in the wavelength range of 800 to 900 nm that were found are described in Table 1.

Example 1-6

In Example 1-1, the compound represented by the formula (1) was replaced with a compound (2) represented by the following formula Compound (2)

Figure 4:
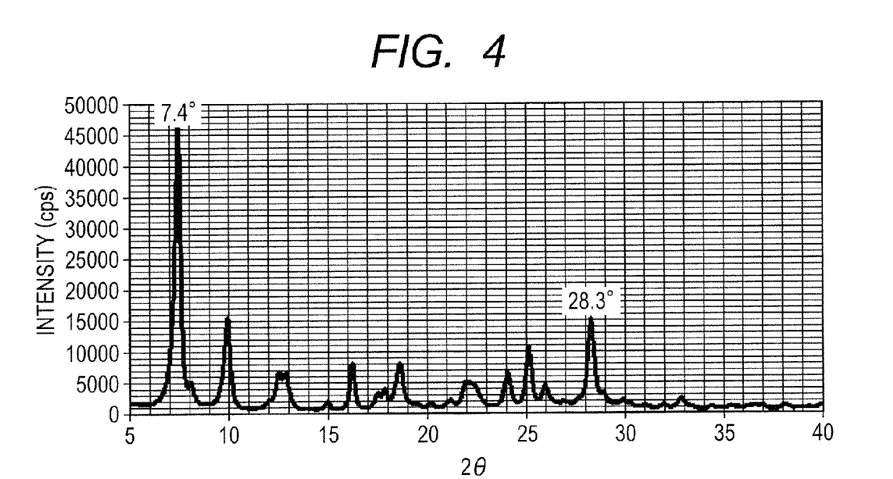
FIG. 4 is a powder X-ray diffraction chart of a hydroxygallium phthalocyanine crystal obtained in Example 1-6.

(product code: M0133, made by Tokyo Chemical Industry Co., Ltd.), and a milling treatment was performed with a ball mill in a high-temperature environment (40° C.), for 200 hours. A hydroxygallium phthalocyanine crystal was obtained in the same treatment as in Example 1-2, except far the above. The powder X-ray diffraction spectrum of the produced crystal is illustrated in FIG. 4. It is found that the crystal has peaks at Bragg angles 2θ±0.2° of 7.4° and 28.3° in CuKα characteristic X-ray diffraction. As a result of the same NMR measurement as in Example 1-1, the compound (2) with a content of 1.3% by mass in the crystal was confirmed.

Example 1-7

Figure 5:
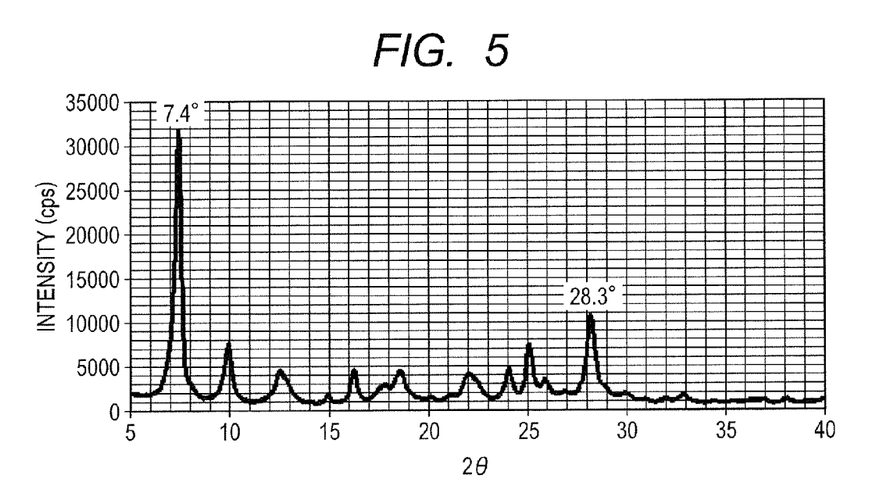
FIG. 5 is a powder X-ray diffraction chart of a hydroxygallium phthalocyanine crystal obtained in Example 1-7.

A hydroxygallium phthalocyanine crystal was obtained in the same manner as in Example 1-6, except that the milling treatment by a ball mill was changed to a milling treatment by a paint shaker (made by Toyo Seiki Seisaku-sho, Ltd.) for 8 hours. The powder X-ray diffraction chart of the produced crystal is illustrated in FIG. 5. It is found that the crystal has peaks at Bragg angles 2θ±0.2° of 7.4° and 28.3° in CuKα characteristic X-ray diffraction. As a result of the same NMR measurement as in Example 1-1, the compound (2) with a content of 1.55% by mass in the crystal was confirmed.

Example 1-8

Except that the compound represented by the formula (1) was changed to a compound (3) represented by the following formula Compound (3)

Figure 6:
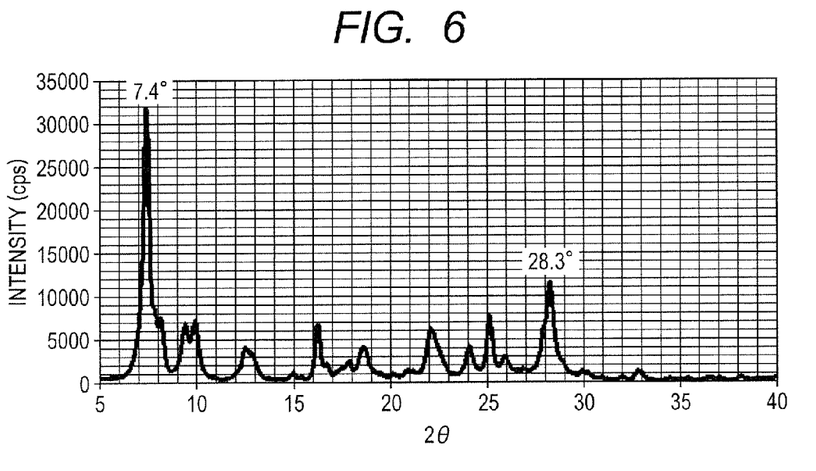
FIG. 6 is a powder X-ray diffraction chart of a hydroxygallium phthalocyanine crystal obtained in Example 1-8.

(product code: M0488, made by Tokyo Chemical Industry Co., Ltd.) in Example 1-4, a hydroxygallium phthalocyanine crystal was obtained in the same treatment as in Example 1-4. The powder X-ray diffraction chart of the produced crystal is illustrated in FIG. 6. It is found that the crystal has peaks at Bragg angles 2θ±0.2° of 7.4° and 28.3° in CuKα characteristic X-ray diffraction. As a result of the same NMR measurement as in Example 1-1, the compound (3) with a content of 1.7% by mass in the crystal was confirmed.

Example 1-9

Figure 7:
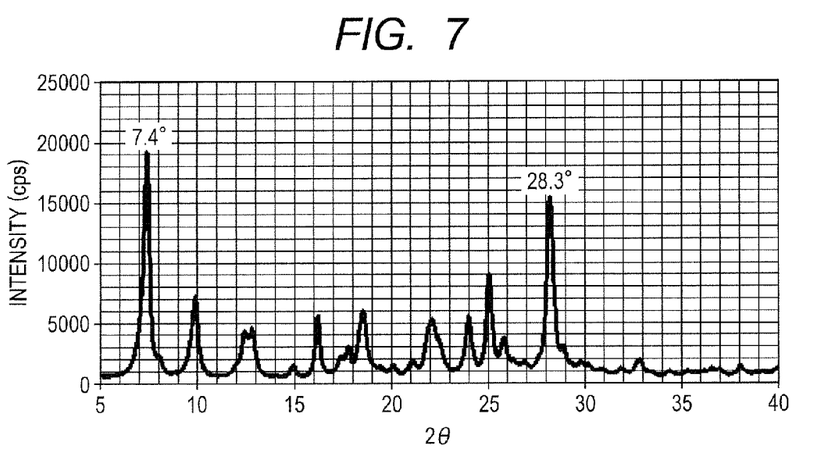
FIG. 7 is a powder X-ray diffraction chart of a hydroxygallium phthalocyanine crystal obtained in Example 1-9.

In Example 1-3, 9.5 parts of the compound represented by the formula (1) was replaced with 4.8 parts of N,N-dimethylformamide (product code: D0722, made by Tokyo Chemical Industry Co., Ltd.) and 4.7 parts of a compound represented by the formula (1). A hydroxygallium phthalocyanine crystal was obtained in the same manner as in Example 1-3, except for the above. The powder X-ray diffraction spectrum of the produced crystal is illustrated in FIG. 7. It is found that the crystal has peaks at Bragg angles 2θ±0.2° of 7.4° and 28.3° in CuKα characteristic X-ray diffraction. As a result of the same NMR measurement as in Example 1-1, the compound (1) with a content of 0.3% by mass in the crystal was confirmed. Using the produced hydroxygallium phthalocyanine crystal, the optical absorption spectrum was also measured. The local maximal peak position in the wavelength range of 600 to 660 nm, and the local maximal peak position in the wavelength range of 800 to 900 nm that were found are described in Table 1.

Example 1-10

Figure 8:
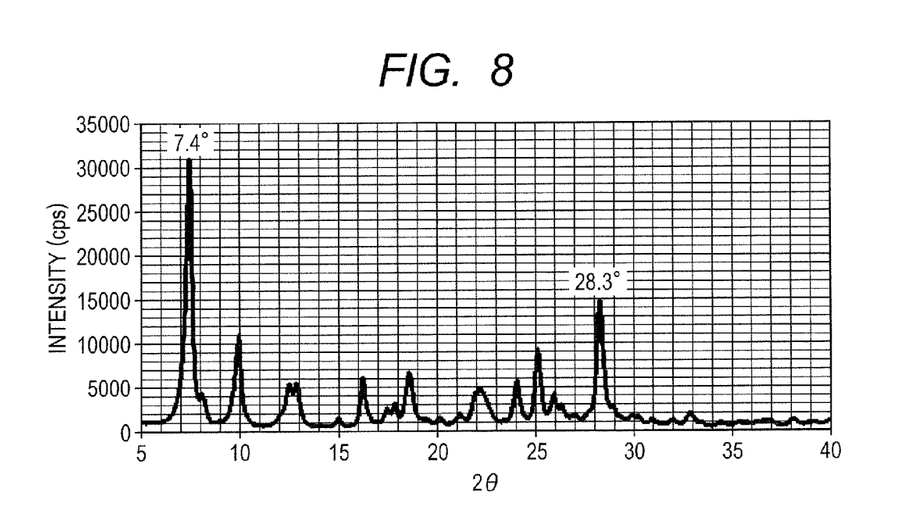
FIG. 8 is a powder X-ray diffraction chart of a hydroxygallium phthalocyanine crystal obtained in Example 1-10.

In Example 1-3, 9.5 parts of the compound represented by the formula (1) was replaced with 7.6 parts of N,N-dimethylformamide (product code: D0722, made by Tokyo Chemical Industry Co., Ltd.) and 1.9 parts of a compound represented by the formula (1). A hydroxygallium phthalocyanine crystal was obtained in the same manner as in Example 1-3, except for the above. The powder X-ray diffraction spectrum of the produced crystal is illustrated in FIG. 8. It is found that the crystal has peaks at Bragg angles 2θ±0.2° of 7.4° and 28.3° in CuKα characteristic X-ray diffraction. As a result of the same NMR measurement as in Example 1-1, the compound (1) with a content of 0.1% by mass in the crystal was confirmed. Using the produced hydroxygallium phthalocyanine crystal, the optical absorption spectrum was also measured. The local maximal peak position in the wavelength range of 600 to 660 nm, and the local maximal peak position in the wavelength range of 800 to 900 nm that were found are described in Table 1.

Comparative Example 1-1

Figure 12:
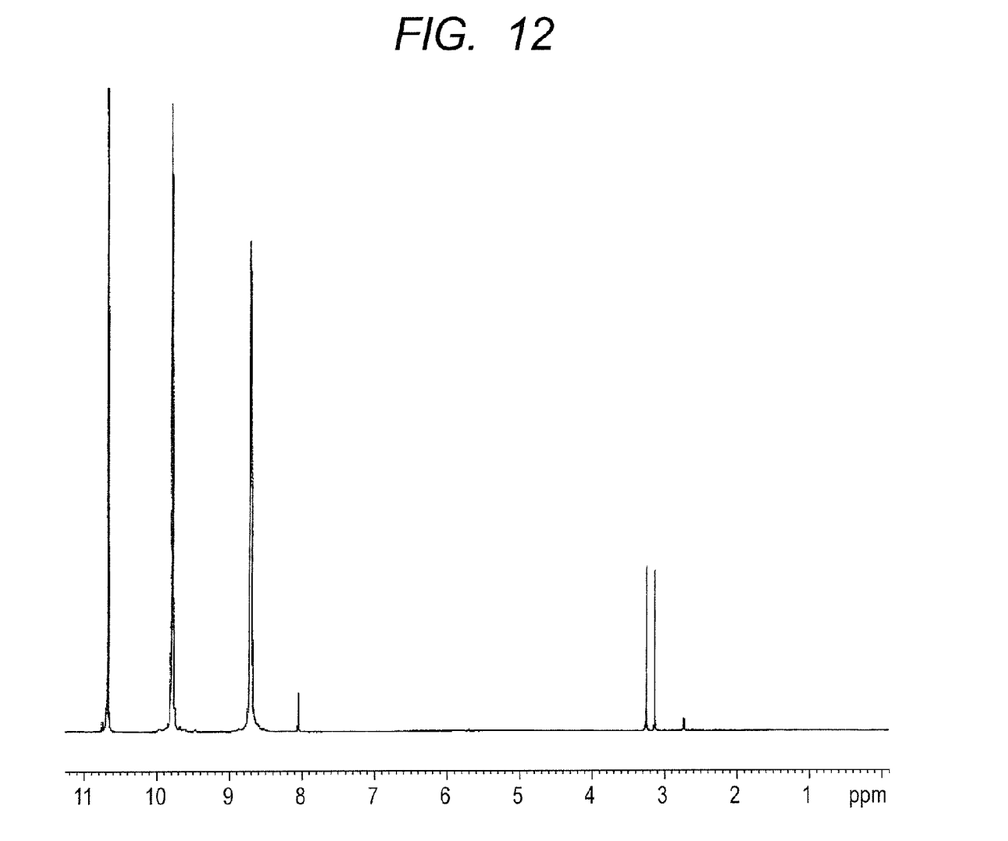
FIG. 12 is a chart illustrating a H-NMR spectrum of a hydroxygallium phthalocyanine crystal obtained in Comparative Example 1-1.

In Example 1-1, 0.5 parts of hydroxygallium phthalocyanine, 9.5 parts of a compound represented by the formula (1), and 15 parts of glass beads having a diameter of 0.8 mm were replaced with 1.25 parts of hydroxygallium phthalocyanine, 9.5 parts of N,N-dimethylformamide, and 25 parts of glass beads having a diameter of 5 mm. In addition, the milling treatment time was changed to 48 hours. Except for the above, a hydroxygallium phthalocyanine crystal was obtained in the same manner as in Example 1-1. In the manufacturing process of the hydroxygallium phthalocyanine crystal, the compound represented by the formula (1) was not used. In the hydroxygallium phthalocyanine crystal obtained in Comparative Example 1-1, therefore, the compound represented by the formula (1) was not contained. As a result of the same NMR measurement as in Example 1-1, N,N-dimethylformamide with a content of 2.1% by mass in the crystal was confirmed. The $^1$H-NMR spectrum of the produced hydroxygallium phthalocyanine crystal is illustrated in FIG. 12.

Comparative Example 1-2

Except that a compound represented by the formula (1) was replaced with N,N-dimethylformamide and the milling treatment time was changed to 100 hours in Example 1-1, a hydroxygallium phthalocyanine crystal was obtained by the same treatment as in Example 1-1. In the manufacturing process of the hydroxygallium phthalocyanine crystal obtained in Comparative Example 1-2, the compound represented by the formula (1) was not used. In the hydroxygallium phthalocyanine crystal obtained in Comparative Example 1-2, therefore, the compound represented by the formula (1) was not contained. As a result of the same NMR measurement as in Example 1-1, N,N-dimethylformamide with a content of 2.1% by mass in the crystal was confirmed. Using the produced hydroxygallium phthalocyanine crystal, the optical absorption spectrum was also measured. The local maximal peak position in the wavelength range of 600 to 660 nm, and the local maximal peak position in the wavelength range of 800 to 900 nm that were found are described in Table 1.

Comparative Example 1-3

Except that the milling treatment time was changed to 100 hours in Example 1-1, a hydroxygallium phthalocyanine crystal was obtained by the same treatment as in Example 1-1. As a result of the same NMR measurement as in Example 1-1, the compound (1) with a content of 2.1% by mass in the crystal was confirmed. Using the produced hydroxygallium phthalocyanine crystal, the optical absorption spectrum was also measured. The local maximal peak position in the wavelength range of 600 to 660 nm, and the local maximal peak position in the wavelength range of 800 to 900 nm that were found are described in Table 1.

Comparative Example 1-4

Except that a compound represented by the formula (1) was replaced with dimethylsulfoxide (product code: D0798, made by Tokyo Chemical Industry Co., Ltd.) and the milling treatment time was changed to 100 hours in Example 1-1, a hydroxygallium phthalocyanine crystal was obtained by the same treatment as in Example 1-1. In the manufacturing process of the hydroxygallium phthalocyanine crystal obtained in Comparative Example 1-4, the compound represented by the formula (1) was not used. In the hydroxygallium phthalocyanine crystal obtained in Comparative Example 1-4, therefore, the compound represented by the formula (1) was not contained. As a result of the same NMR measurement as in Example 1-1, N,N-dimethylsulfoxide with a content of 2.4% by mass in the crystal was confirmed.

Comparative Example 1-5

Except that the compound represented by the formula (1) was replaced with 1-methyl-2-pyrolidone (product code: M0418, made by Tokyo Chemical Industry Co., Ltd.) and the milling treatment time was changed to 100 hours in Example 1-1, a hydroxygallium phthalocyanine crystal was obtained by the same treatment as in Example 1-1. In the manufacturing process of the hydroxygallium phthalocyanine crystal obtained in Comparative Example 1-5, the compound represented by the formula (1) was not used. In the hydroxygallium phthalocyanine crystal obtained in Comparative Example 1-5, therefore, the compound represented by the formula (1) was not contained. As a result of the same NMR measurement as in Example 1-1, 1-methyl-2-pyrolidone with a content of 2.9% by mass in the crystal was confirmed.

Comparative Example 1-6

Together with 300 parts of glass beads having a diameter of 1.0 mm, 7 parts of hydroxygallium phthalocyanine obtained in Example 1-1 and 210 parts of N,N-dimethylformamide were subjected to milling treatment at room temperature (23° C.) for 5 hours. A hydroxygallium phthalocyanine crystal was produced from the dispersion liquid using tetrahydrofuran. In filtration, the strainer was sufficiently cleaned with tetrahydrofuran. The filter residue was vacuum dried so that 5.2 parts of hydroxygallium phthalocyanine crystal were obtained. In the manufacturing process of the hydroxygallium phthalocyanine crystal, the compound represented by the formula (1) was not used. In the hydroxygallium phthalocyanine crystal obtained in Comparative Example 1-6, therefore, the compound represented by the formula (1) was not contained. As a result of the same NMR measurement as in Example 1-1, N,N-dimethylformamide with a content of 2.4% by mass in the crystal was confirmed.

Comparative Example 1-7

Except that a compound represented by the formula (1) was replaced with N,N-dimethylformamide and the milling treatment time was changed to 200 hours in Example 1-1, a hydroxygallium phthalocyanine crystal was obtained by the same way as in Example 1-1. In the manufacturing process of the hydroxygallium phthalocyanine crystal, the compound represented by the formula (1) was not used. In the hydroxygallium phthalocyanine crystal obtained in Comparative Example 1-7, therefore, the compound represented by the formula (1) was not contained. As a result of the same NMR measurement as in Example 1-1, N,N-dimethylformamide with a content of 1.85% by mass in the crystal was confirmed. Using the produced hydroxygallium phthalocyanine crystal, the optical absorption spectrum was also measured. The local maximal peak position in the wavelength range of 600 to 660 nm, and the local maximal peak position in the wavelength range of 800 to 900 nm that were found are described in Table 1.

Comparative Example 1-8

Except that a compound represented by the formula (1) was replaced with N,N-dimethylformamide and the milling treatment time was changed to 300 hours in Example 1-1, a hydroxygallium phthalocyanine crystal was obtained by the same manner as in Example 1-1. In the manufacturing process of the hydroxygallium phthalocyanine crystal obtained in Comparative Example 1-8, the compound represented by the formula (1) was not used. In the hydroxygallium phthalocyanine crystal obtained in Comparative Example 1-8, therefore, the compound represented by the formula (1) was not contained. As a result of the same NMR measurement as in Example 1-1, N,N-dimethylformamide with a content of 1.7% by mass in the crystal was confirmed. Using the produced hydroxygallium phthalocyanine crystal, the optical absorption spectrum was also measured. The local maximal peak position in the wavelength range of 600 to 660 nm, and the local maximal peak position in the wavelength range of 800 to 900 nm that were found are described in Table 1.

Example 2-1

Firstly, a solution including 60 parts of barium sulfate particles coated with tin oxide (trade name: Passtran PC1, made by Mitsui Mining & Smelting Co., Ltd.), 15 parts of titanium oxide particles (trade name: TITANIX JR, made by Tayca Corporation), 43 parts of a resol-type phenol resin (trade name: Phenolite J-325 made by DIC Corporation, solid content: 70% by mass), 0.015 parts of silicone oil (trade name: SH28PA, made by Dow Corning Toray Co., Ltd.), 3.6 parts of silicone resin (trade name: Tospearl 120, made by Momentive Performance Materials Japan LLC.), 50 parts of 2-methoxy-1-propanol, and 50 parts of methanol was put in a ball mill, and dispersed for 20 hours so as to prepare a coating liquid for forming a conductive layer.

The coating liquid for forming a conductive layer was applied on aluminum cylinder (diameter: 24 mm) as a support with immersion coating, and the produced coating film was dried at 140° C. for 30 minutes so that a conductive layer having a film thickness of 15 µm was formed.

Subsequently 10 parts of copolymer nylon resin (trade name: Amilan CM8000, made by Toray Industries, Inc.) and 30 parts of methoxymethylated 6-nylon resin (trade name: Tresin EF-30T, made by Nagase Chemtex Corporation) were dissolved in a mixed solvent of 400 parts of methanol and 200 parts of n-butanol so as to prepare a coating liquid for forming an undercoat layer.

The coating liquid for forming an undercoat layer was applied to the conductive layer with immersion coating, and the produced coating film was dried so that an undercoat layer having a film thickness of 0.5 µm was formed.

Subsequently, 10 parts of the hydroxygallium phthalocyanine crystal (charge generating substance) produced in Example 1-1, 5 parts of polyvinylbutyral (trade name: S-LEC BX-1, made by Sekisui Chemical Co., Ltd.), and 250 parts of cyclohexanone were put in a sand mill with glass beads having a diameter of 1 mm for dispersion treatment for 1 hours. To the dispersion liquid, 250 parts of ethyl acetate was added to dilute it, thereby preparing a for forming a charge generation layer.

The coating liquid for forming a charge generation layer was applied to the undercoat layer with immersion coating. The produced coating film was dried at 100° C. for 10 minutes to form the charge generation layer having a film thickness of 0.20 µm.

Subsequently, 8 parts of a compound (charge transporting substance) represented by the following formula (4) and 10 parts of polycarbonate (trade name: Iupilon Z-200, made by Mitsubishi Engineering-Plastics Corporation) were dissolved in 80 parts of monochlorobenzene so as to prepare a coating liquid for forming a charge transport layer.

The coating liquid for forming a charge transport layer was applied to the charge generation layer by immersion coating. The produced coating film was dried at 110° C. for 1 hour to form a charge transport layer having a film thickness of 16 μm.

The electrophotographic photosensitive member of Example 2-1 in a cylindrical shape (drum shape) was thus manufactured.

Examples 2-2 to 2-10

Except that the hydroxygallium phthalocyanine crystal in preparing the coating liquid for forming a charge generation layer in Example 2-1 was replaced with the hydroxygallium phthalocyanine crystals produced in Examples 1-2 to 1-10, the electrophotographic photosensitive members in Examples 2-2 to 2-10 were made in the same way as in Example 2-1.

Comparative Examples 2-1 to 2-8

Except that the hydroxygallium phthalocyanine crystal in preparing the coating liquid for forming a charge generation layer in Example 2-1 was replaced with the hydroxygallium phthalocyanine crystals produced in Comparative Examples 1-1 to 1-8, the electrophotographic photosensitive members in Comparative Examples 2-1 to 2-8 were made in the same way as in Example 2-1.

Evaluation of Examples 2-1 to 2-10 and Comparative Examples 2-1 to 2-8

The electrophotographic photosensitive members in Examples 2-1 to 2-10 and Comparative Examples 2-1 to 2-8 were evaluated on the ghost image in a normal temperature and normal humidity environment at a temperature of 23° C. and a humidity of 50% RH.

A laser beam printer made by Hewlett Packard Company (trade name: Color Laser Jet CP3525dn) was modified to use as an electrophotographic apparatus for evaluation. As a result of modification, a pre-exposing light was unlit and charging conditions and the amount of laser exposure were variably controlled. In addition, a manufactured electrophotographic photosensitive member was mounted in a process cartridge for cyan color and attached to the station of the process cartridge for cyan, allowing for operation without mounting of process cartridges for other colors to the laser beam printer main body.

In outputting an image, the process cartridge for cyan color alone was attached to the laser beam printer main body so that a single color image was outputted using cyan toner alone. The surface potential of the electrophotographic photosensitive member was initially set at −500 V for a dark part and −100 V for a bright part. In the measurement of the surface potential of the electrophotographic photosensitive member for potential setting, a potential probe (trade name: Model 6000B-8, made by Trek Japan Co., Ltd.) mounted at the development position of the process cartridge was used. The potential at the center of an electrophotographic photosensitive member in the longitudinal direction was measured with a surface potential meter (trade name: Model 344, made by Trek Japan Co., Ltd).

Figure 9:
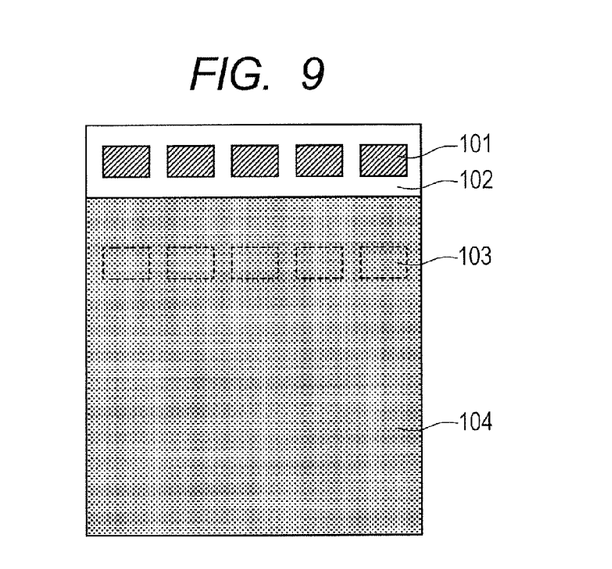
FIG. 9 is a view illustrating a ghosting evaluation image, for use in ghost image evaluation.
Figure 10:
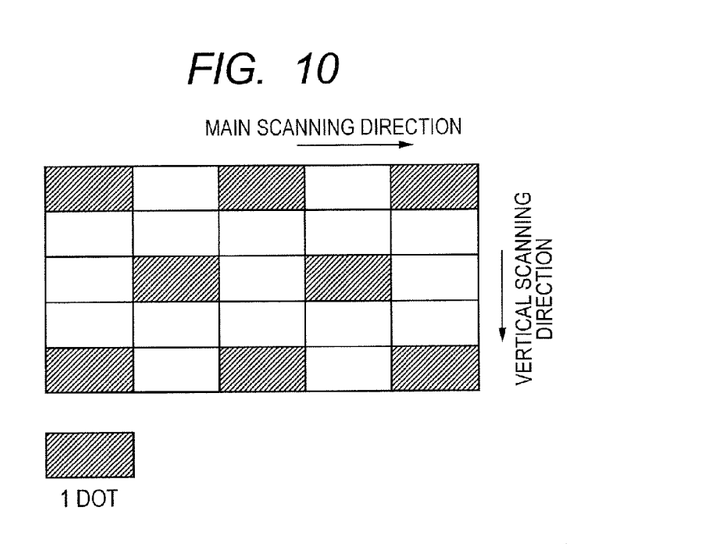
FIG. 10 is a view illustrating a one-dot Keima pattern.

As illustrated in FIG. 9, a ghosting evaluation image was formed by outputting square images with a solid black 101 in a white solid 102 at the head portion of an image and then outputting a half-tone image 104 with a one-dot Keima pattern illustrated in FIG. 10. A solid white image was outputted on a first sheet, and then 5 sheets of the ghosting evaluation image were outputted in succession. Subsequently a solid black image is outputted on one sheet, and then 5 sheets of the ghosting evaluation image were outputted once again. The images were outputted in this order and evaluation was performed based on the total 10 sheets of the ghosting evaluation image.

The difference in image density between the one-dot Keima pattern and the ghost part (a portion 103 where ghosting may occur resulting from the solid black 101) was measured with a spectral densitometer (trade name: X-Rite 504/508, made by X-Rite Inc.) so as to evaluate ghosting. The measurement was performed at 10 points for one sheet of ghost evaluation image. The average of the 10 points was assumed to be the result of the one sheet of ghosting evaluation images. All of the 10 ghosting evaluation images were measured in the same manner, and then the average value thereof was obtained as the difference in density for each example. The smaller the difference in density is, the smaller the degree of ghosting is, achieving better results. The results are described in Table 1.

As clearly shown in Examples 2-1 to 2-10 and Comparative Examples 2-1 to 2-8, an electrophotographic photosensitive member including a phthalocyanine crystal in which a compound represented by formula (1), (2), or (3) is contained in an amount of 0.1% by mass or more and 1.7% by mass or less based on a phthalocyanine in the phthalocyanine crystal can provide an image with positive ghosting being suppressed.

TABLE 1

|  | Contained compound | Content % by weight % | Density difference in ghost image | Local maximal peak position in 600 to 660 nm wavelength range | Local maximal peak position in 800 to 900 nm wavelength range |
| --- | --- | --- | --- | --- | --- |
| Example 2-1 | Compound (1) | 0.9 | 0.029 | 644 | 816 |
| Example 2-2 | Compound (1) | 1.7 | 0.034 | 640 | 827 |
| Example 2-3 | Compound (1) | 0.7 | 0.028 | 646 | 814 |
| Example 2-4 | Compound (1) | 0.55 | 0.026 | 647 | 811 |
| Example 2-5 | Compound (1) | 1.6 | 0.032 | 642 | 825 |
| Example 2-6 | Compound (2) | 1.3 | 0.036 | — | — |
| Example 2-7 | Compound (2) | 1.55 | 0.035 | — | — |
| Example 2-8 | Compound (3) | 1.7 | 0.039 | — | — |
| Example 2-9 | Compound (1) | 0.3 | 0.030 | 643 | 815 |
| Example 2-10 | Compound (1) | 0.1 | 0.036 | 641 | 816 |
| Comparative Example 2-1 | — | — | 0.046 | — | — |
| Comparative | — | — | 0.045 | 638 | 834 |

TABLE 1-continued

| | Contained compound | Content % by weight % | Density difference in ghost image | Local maximal peak position in 600 to 660 nm wavelength range | Local maximal peak position in 800 to 900 nm wavelength range |
|---|---|---|---|---|---|
| Example 2-2 Comparative Example 2-3 | Compound (1) | 2.1 | 0.043 | 638 | 828 |
| Comparative Example 2-4 | — | — | 0.048 | — | — |
| Comparative Example 2-5 | — | — | 0.051 | — | — |
| Comparative Example 2-6 | — | — | 0.047 | — | — |
| Comparative Example 2-7 | — | — | 0.045 | 638 | 830 |
| Comparative Example 2-8 | — | — | 0.043 | 638 | 829 |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-094020, filed Apr. 30, 2014 and Japanese Patent Application No. 2015-072648, filed Mar. 31, 2015 which are hereby incorporated by reference herein in their entirety.

What is claimed is:

1. An electrophotographic photosensitive member comprising:
a support; and
a photosensitive layer on the support, the photosensitive layer comprising a phthalocyanine crystal containing a compound represented by formula (1), (1)

wherein X represents a hydrogen atom or an alkyl group having 1 or 2 carbon atoms, and
the content of the compound represented by formula (1) is 0.1 to 1.7% by mass based on a phthalocyanine in the phthalocyanine crystal.

2. The electrophotographic photosensitive member according to claim 1, wherein the phthalocyanine crystal is a gallium phthalocyanine crystal.

3. The electrophotographic photosensitive member according to claim 2, wherein the gallium phthalocyanine crystal is a hydroxygallium phthalocyanine crystal.

4. The electrophotographic photosensitive member according to claim 3, wherein the hydroxygallium phthalocyanine crystal has peaks at Bragg angles $2\theta \pm 0.2°$ of 7.4° and 28.3° in CuKα characteristic X-ray diffraction.

5. The electrophotographic photosensitive member according to claim 1, wherein the content of the compound represented by formula (1) is 0.2 to 1.2% by mass based on the phthalocyanine in the phthalocyanine crystal.

6. The electrophotographic photosensitive member according to claim 1, wherein X is a hydrogen atom.

7. The electrophotographic photosensitive member according to claim 3, wherein the hydroxygallium phthalocyanine crystal has a local maximal peak in the range of 642 to 650 nm in an optical absorption spectrum.

8. The electrophotographic photosensitive member according to claim 7, wherein the hydroxygallium phthalocyanine crystal has a local maximal peak in the range of 810 to 820 nm in the optical absorption spectrum.

9. The electrophotographic photosensitive member according to claim 1, wherein the phthalocyanine crystal comprises N,N-dimethylformamide.

10. A process cartridge which integrally supports: an electrophotographic photosensitive member according to claim 1; and at least one unit selected from the group consisting of a charging unit, a developing unit, a transfer unit and a cleaning unit, the cartridge being detachably mountable to a main body of an electrophotographic apparatus.

11. An electrophotographic apparatus comprising:
an electrophotographic photosensitive member according to claim 1; with
a charging unit, an exposing unit, a developing unit and a transfer unit.

12. A phthalocyanine crystal comprising a compound represented by formula (1)

(1)

wherein X represents a hydrogen atom or an alkyl group having 1 or 2 carbon atoms, and
the content of the compound represented by formula (1) is 0.1 to 1.7% by mass based on a phthalocyanine in the phthalocyanine crystal.

13. The phthalocyanine crystal according to claim 12, wherein the content of the compound represented by formula (1) is 0.2 to 1.2% by mass based on a phthalocyanine in the phthalocyanine crystal.

14. A manufacturing method of the phthalocyanine crystal according to claim 12, comprising transforming the phthalocyanine crystal by adding the compound represented by formula (1) to a phthalocyanine followed by milling treatment.

15. The manufacturing method of the phthalocyanine crystal according to claim 14, further comprising obtaining the phthalocyanine by an acid pasting method prior to the step of transforming the phthalocyanine crystal.

16. The manufacturing method of the phthalocyanine crystal according to claim 14, wherein a time period for the milling treatment is 200 hours or more.

17. A manufacturing method of an electrophotographic photosensitive member having a support and a photosensitive layer formed on the support, comprising:
   manufacturing the phthalocyanine crystal by the manufacturing method according to claim 14; and
   forming a coating film from a coating liquid for forming the photosensitive layer which contains the phthalocyanine crystal, and then drying the coating film to form the photosensitive layer.

18. A manufacturing method of an electrophotographic photosensitive member having a support, a charge generation layer formed on the support, and a charge transport layer formed on the charge generation layer, comprising:
   manufacturing the phthalocyanine crystal by the manufacturing method according to claim 14; and
   forming a coating film from a coating liquid for forming a charge generation layer which contains the phthalocyanine crystal, and then drying the coating film to form the charge generation layer.

* * * * *